(12) United States Patent
Venturini et al.

(10) Patent No.: US 12,256,960 B2
(45) Date of Patent: Mar. 25, 2025

(54) QUICK ATTACHMENT CLAMP FOR EXTERNAL FIXATION SYSTEMS

(71) Applicant: ORTHOFIX S.R.L., Bussolengo (IT)

(72) Inventors: Daniele Venturini, Povegliano Veronese (IT); Enrico Zandoná, Quinto di Valpantena (IT); Andrea Ottoboni, Giacciano con Baruchella (IT)

(73) Assignee: Orthofix S.R.L., Bussolengo (IT)

( * ) Notice: Subject to any disclaimer, the term of this patent is extended or adjusted under 35 U.S.C. 154(b) by 504 days.

(21) Appl. No.: 17/613,273

(22) PCT Filed: May 27, 2020

(86) PCT No.: PCT/EP2020/064658
§ 371 (c)(1),
(2) Date: Nov. 22, 2021

(87) PCT Pub. No.: WO2020/239815
PCT Pub. Date: Dec. 3, 2020

(65) Prior Publication Data
US 2022/0226022 A1     Jul. 21, 2022

(30) Foreign Application Priority Data
May 27, 2019   (IT) ........................ 102019000007314

(51) Int. Cl.
*A61B 17/64*     (2006.01)
(52) U.S. Cl.
CPC ................................ *A61B 17/6466* (2013.01)
(58) Field of Classification Search
CPC ........ A61B 17/64–6491; A61B 17/7049–7052
See application file for complete search history.

(56) References Cited

U.S. PATENT DOCUMENTS

| 4,483,334 A | 11/1984 | Murray |
| 4,920,959 A | 5/1990 | Witzel et al. |

(Continued)

FOREIGN PATENT DOCUMENTS

| EP | 1184000 A1 | 3/2002 |
| JP | 2010540112 A | 12/2010 |

(Continued)

OTHER PUBLICATIONS

International Searching Authority/European Patent Office, "International Search Report," for PCT/EP2020/064658, mailed Sep. 4, 2020, 3 pages.

(Continued)

*Primary Examiner* — Jan Christopher L Merene
*Assistant Examiner* — Steven J Cotroneo
(74) *Attorney, Agent, or Firm* — Haynes and Boone, LLP

(57) ABSTRACT

A clamp for an external fixator, preferably of the quick attachment type comprises at least one first attachment provided with at least one bar housing seat for a bar of the external fixator and/or with at least one screw housing seat for a bone screw; at least one second attachment provided with at least one bar housing seat; a connector which, in a tightened configuration, passes through said first attachment and said second attachment locking the bars and/or bone screws within the bar housing seats and/or the screw housing seats; and which, in an open configuration, frees the entrance to at least the bar housing seat of said second attachment; and auxiliary connection means between said first attachment and said second attachment which are active in said open configuration.

10 Claims, 13 Drawing Sheets

(56) References Cited

U.S. PATENT DOCUMENTS

| | | |
|---|---|---|
| 5,545,162 A | 8/1996 | Huebner |
| 7,708,736 B2 | 5/2010 | Mullaney |
| 7,938,829 B2 | 5/2011 | Mullaney |
| 8,241,285 B2 | 8/2012 | Mullaney |
| 8,388,619 B2 | 3/2013 | Mullaney |
| 8,734,446 B2 * | 5/2014 | Miller ................ A61B 17/6466 606/59 |
| 8,840,611 B2 | 9/2014 | Mullaney et al. |
| 9,138,260 B2 | 9/2015 | Miller et al. |
| 9,277,937 B2 | 3/2016 | Mullaney |
| 9,532,805 B2 | 1/2017 | Mullaney et al. |
| 9,675,383 B2 | 6/2017 | Mullaney |
| 9,750,535 B2 | 9/2017 | Mullaney |
| 9,883,890 B2 | 2/2018 | Miller et al. |
| 9,888,943 B2 | 2/2018 | Mullaney |
| 10,485,586 B2 | 11/2019 | Miller et al. |
| 10,531,896 B2 * | 1/2020 | Mannanal ............... A61B 17/66 |
| 2002/0077629 A1 | 6/2002 | Hoffman et al. |
| 2003/0069580 A1 | 4/2003 | Langmaid et al. |
| 2006/0039750 A1 * | 2/2006 | Thomke ................ A61B 17/645 403/385 |
| 2007/0049930 A1 | 3/2007 | Hearn et al. |
| 2007/0162008 A1 * | 7/2007 | Cline, Jr. ............ A61B 17/7041 606/60 |
| 2009/0299368 A1 | 12/2009 | Bauer |
| 2009/0306661 A1 * | 12/2009 | Thomke ................ A61B 17/645 606/53 |
| 2011/0112533 A1 * | 5/2011 | Venturini ........... A61B 17/6466 606/54 |
| 2012/0029571 A1 * | 2/2012 | Schwab ................ A61B 17/705 606/278 |
| 2012/0150182 A1 * | 6/2012 | Dominik ................ A61B 17/60 606/59 |
| 2013/0144289 A1 * | 6/2013 | Dorawa ................ A61B 17/60 606/54 |
| 2015/0308478 A1 | 10/2015 | Oesch et al. |
| 2019/0110814 A1 * | 4/2019 | Nemovicher .......... A61B 90/57 |
| 2019/0298422 A1 * | 10/2019 | Rezach ............. A61B 17/7002 |

FOREIGN PATENT DOCUMENTS

| | | |
|---|---|---|
| JP | 2011098201 A | 5/2011 |
| JP | 2014503265 A | 2/2014 |

OTHER PUBLICATIONS

Colombian Patent Office, Colombian Office Action, Reference No. NC/2021/0016740, Jan. 30, 2024, 8 pages.

Japanese Patent Office, Japanese Office Action, Reference No. 2021-570475, 4 pages.

* cited by examiner

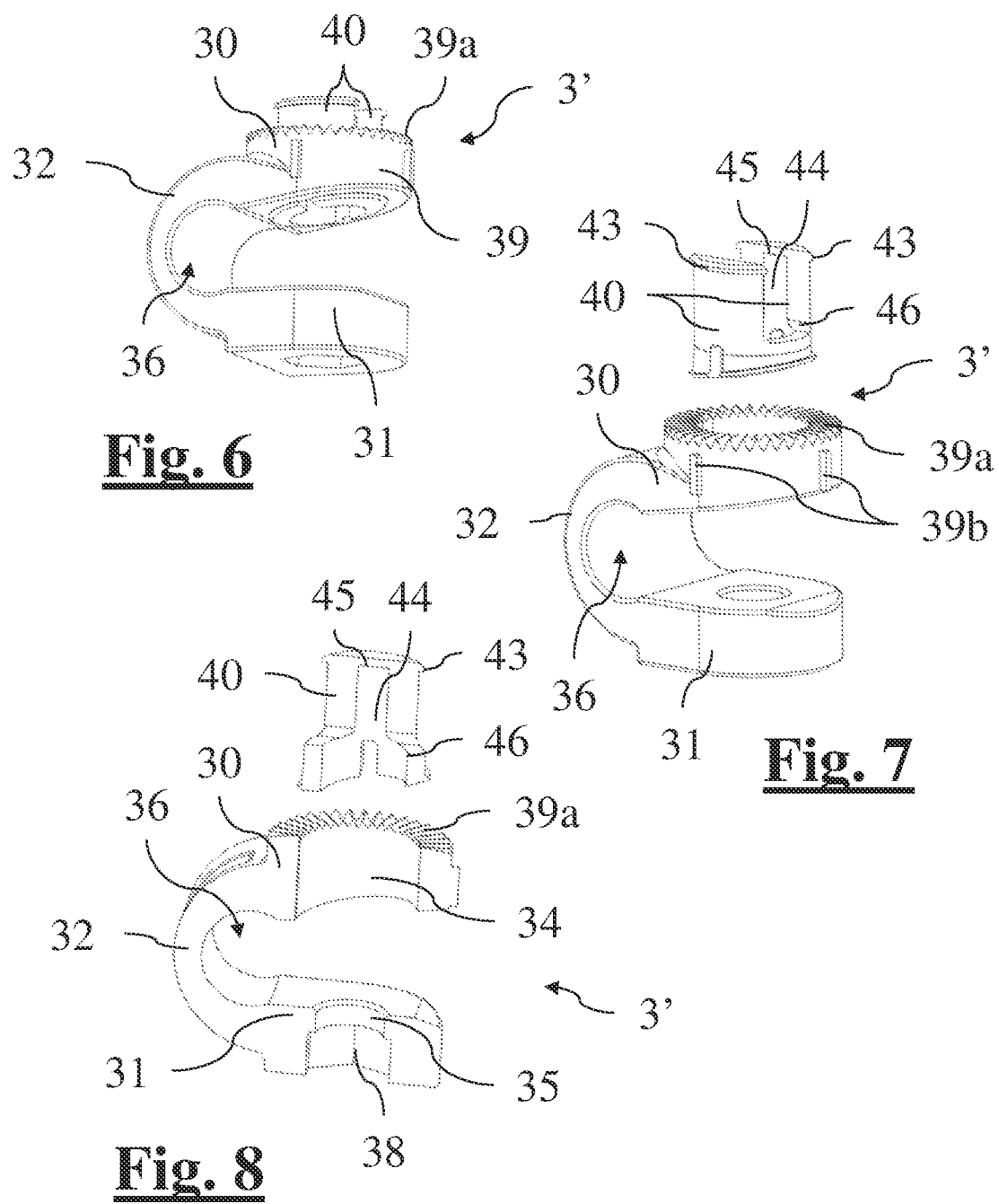

QUICK ATTACHMENT CLAMP FOR EXTERNAL FIXATION SYSTEMS

CROSS-REFERENCE TO RELATED APPLICATION(S)

The present application claims priority under 35 U.S.C. 365 to International Patent Application No. PCT/EP2020/064658, filed May 27, 2020, entitled "Quick Attachment Clamp for External Fixation Systems", which claims priority to Italian patent Application No. 102019000007314, filed May 27, 2019, both of which are incorporated herein by reference into the present application fully set forth herein.

FIELD OF APPLICATION

The present invention relates to a clamp for orthopaedic applications, particularly intended for the coupling of the elements which constitute an external fixation system.

The invention thus finds a useful application in the sector of orthopaedic surgery, particularly trauma surgery.

BACKGROUND

In orthopaedics, external fixation techniques for the stabilization, reduction and manipulation of bone segments are usually employed. These techniques provide the surgical application of a rigid exoskeleton, in the simplest form thereof consisting of a set of bars articulated with each other by means of suitable clamps, associated by means of screws to the patient's bone structure. The adopted mechanical system is globally called external fixator.

The diversity of the therapeutic needs which compose the hospital reality has contributed to the differentiation of various types of fixators, each having technical and morphological features suited for the use it is intended for. Thus, for certain applications, mostly trauma ones and having an urgent nature, the so-called quick fixators have been developed, precisely because they are characterized by fixation simplicity and speed.

Quick fixators comprise structural bars connected to clamps of various kinds: intended to connect the bars to each other in the structure joints (bar-bar clamps); or in charge of associating the bars to through screws which are not anchored to the patient's bone (bar-screw clamps). All these clamps are elements having a particular design criticality, having to reconcile the opposite needs of ease of tightening and fixation stability.

In this context, quick fixation systems were proposed on the market, comprising a plurality of components which can be variously assembled to meet specific surgical needs.

In particular, these systems provide attachments of a different type, for example bar attachments and screw attachments, which can be connected to each other by means of connection screws. The surgeon must hence compose at least two attachments and a connection screw to make a clamp. In these systems, the bar attachments are generally C-shaped; the bar is introduced between the two arms of the C, wherein it is locked by tightening the connection screw.

The systems of the above-described type, although performing in a satisfactory manner the function they are in charge of, have nevertheless some drawbacks that are unsolved to date.

A first drawback relates to the insertion of the bar during surgery. The side insertion, i.e. the insertion transversely to the bar extension, is generally easier than a longitudinal insertion, in particular in case a further intermediate screw is to be added in an implant where two bone screws are already fixed on the same stump. The side insertion is also preferred where the bar has a considerable axial extension and the alignment of the different clamps supporting it is to be checked during surgery. With the C-shaped systems of the known type, the side insertion requires however the extraction of the connection screw which holds together the attachments of the clamp: it is therefore necessary to totally disassemble the clamp and tighten again the assembly after the insertion of the bar. In some cases, the arms of the bar attachment are kept separated by a spacer, which must be removed and reinserted to allow the insertion of the bar. Hence the side insertion turns out to be a complex operation and which would require a considerable time consumption to the surgeon during surgery.

A second drawback always arises from the need to disassemble the device in certain applications. This operation has indeed a risk of fall and/or loss of the single components, a particularly critical risk where the disassembly must be performed during surgery.

A third drawback is the weight of the fixator composed of the sum of bars and clamps, mostly due to the type of material being employed.

A further drawback results from the significant number of pieces composing the clamp, which results in high manufacturing costs of the assembly.

The technical problem underlying the present invention is therefore to solve at least some of the drawbacks reported in the prior art, and in particular to provide a clamp which makes the implant of the external fixator on a patient simpler and less risky.

SUMMARY OF THE INVENTION

The solution idea underlying the present invention is to provide auxiliary connection means which keep the clamp cohesive in an open configuration to allow the side insertion of a bar, in which the surgeon can operate on the components of the clamp before performing the tightening.

The above technical problem is hence solved by a clamp for an external fixator, preferably of the quick attachment type, comprising: at least one first attachment provided with at least one bar housing seat for a bar of the external fixator and/or with at least one screw housing seat for a bone screw; at least one second attachment provided with at least one bar housing seat; and a connector which, in a tightened configuration, passes through said first attachment and said second attachment making them integral with each other and locking the bars and/or bone screws within the bar housing seats and/or the screw housing seats; the clamp being further configurable in an open configuration, wherein said connector is at least partially extracted from said second attachment, thus freeing a side entrance to said bar housing seat, said clamp comprising auxiliary connection means which keep said first attachment and said second attachment interconnected in said open configuration.

Thanks to the device adopted, the clamp can therefore take a steady and cohesive open configuration; in particular, this open configuration can allow the side entrance to at least one of the bar housing seats which are usually closed by the connector.

The side entrance is particularly advantageous since it helps the orthopaedic surgeon in aligning the consecutive clamps which must hold a bar, especially where this bar is held by more than two aligned clamps.

Moreover, the cohesion of the clamp in the open configuration prevents losses or falls of the single components, making the manipulation of the clamp easier and safer, mainly during surgery.

Preferably, the connector comprises a head which is accessible to the user at a first end of the clamp and a stem provided with at least one threaded portion; said clamp comprising a threaded seat located at the second end thereof; in the tightened configuration, the stem passes through said first attachment and said second attachment and the threaded portion engages in the threaded seat, locking the bars and/or bone screws within the bar housing seats and/or the screw housing seats; in the open configuration, said threaded portion is totally disengaged from the threaded seat.

Still preferably, the first end of the clamp is on the side of the first attachment, the second end of the clamp is on the side of the second attachment, the second attachment comprises two arms, connected by a C-shaped flexible bridge which defines the bar housing seat; in the tightened configuration, said stem extends between the two arms interfering with the side entrance to the bar housing seat; in the open configuration, said stem rises in the direction of the first attachment, thus freeing the side entrance to the bar housing seat.

The connector can advantageously comprise a stop collar arranged along the stem—preferably at the end of the threaded portion—to limit the maximum tightening of the clamp. In this way, the excessive deformation of the single attachments is avoided without having to resort to separate spacers, which are potentially losable and complex to position.

The stop collar has preferably two plane surfaces jointed by a truncated conical portion, arranged to be introduced into a corresponding truncated conical seat of the second attachment.

Moreover, the stop collar can prevent the complete extraction of the connector from the rest of the clamp in the open configuration, interfering with a holding member which is integral with one of the attachments of the clamp itself.

The above auxiliary connection means can advantageously allow, in the open configuration, a relative axial movement of the second attachment with respect to the first attachment, between: a first position, in which two coupling surfaces provided on the first attachment and on the second attachment, respectively, are mutually engaged in contact preventing the relative rotation of the first attachment with respect to the second attachment; and a second position, in which said coupling surfaces are spaced apart and the relative rotation of the first attachment with respect to the second attachment is allowed. The orthopaedic surgeon is thus allowed to operate on the relative orientation of the two attachments in the open configuration.

The aforesaid coupling surfaces can comprise radial toothing or serrations, or other elements arranged to mutually engage in a side-by-side position.

The above-mentioned auxiliary connection means can comprise at least one tongue, which is integral with one of the first attachment and second attachment, and at least one coupling seat which is integral with the other of the first attachment and second attachment, said at least one tongue being axially sliding within said coupling seat up to reach a maximum extension lock, said at least one tongue being further rotatable within said coupling seat with respect to an axis of rotation.

Preferably, the tongues are integral with the second attachment while the coupling seat is obtained on the first attachment.

The maximum extension lock is preferably defined by a narrowing of the coupling seat against which a tooth protruding outwards of said at least one tongue abuts.

The tongues are preferably a plurality, arranged along a circumference centred in the axis of rotation, and being deformable inwards to allow the snap coupling within the coupling seat.

Still preferably, the tongues are two, being opposed to each other.

The axial deviation between the attachments allowed by the auxiliary connection means is preferably such as to allow the tongues to be accessed by the operator. By pressing the tongues from two opposed sides, the operator bends them inwards allowing the auxiliary connection means to be released.

Preferably, the tongue or the tongues are integral with the second attachment, and they define a lock to the extraction of the connector in the open configuration.

Preferably, the above-mentioned locking action is performed by a limit stop located at the end of the tongues and opposed to the teeth of the tongues themselves, which holds the stop collar of the connector. Given the flexibility of the tongues, the connector can be forced beyond the limit stop when they are free to bend outwards. But this outward bending is not allowed when the auxiliary connection means are coupled; under this condition, the tooth of the tongue is externally abutting against an internal surface of the coupling seat.

Thanks to the above device, the extraction of the fixator turns out to be possible, but subordinate to the disconnection of the two attachments which compose the clamp.

The limit stop is preferably at the end of a cylindrical track made on an internal surface of the tongue or of the tongues.

The tongue or the tongues can be made integrally with one of the two attachments of the connector, preferably the second attachment; as an alternative, they can be made on a separate insert, which is introduced into a central hole of the attachment.

Preferably, the first attachment comprises at least two screw housing seats, arranged to allow the tightening of bone screws of different diameter so as to be able to serve the different anatomical sites or different dimensions of the bones (for example: 4 mm for wrist, foot; 5 mm for humerus, ankle; 6 mm for pelvis, femur, tibia).

Still preferably, a first seat can be arranged to selectively house two different diameters (for example: 5 mm and 6 mm); a second seat can be arranged to house a third diameter (for example: 4 mm).

Preferably, the first attachment comprises both the screw housing seats and the bar housing seat. The possibility of combined bar/screw attachment allows flexibility when using the clamp, besides considerably facilitating the assembly given that a single component can be selected for different uses.

The connector preferably provides, at an end of the stem, a coupling profile for a tightening tool—preferably a polygonal recess for a wrench head, for example an hexagonal recess for a setscrew wrench—and a tightening knob for the manual tightening of the connector.

The tightening knob can thus be advantageously used in a preliminary tightening step, allowing an ergonomic assembly of the system.

The material of the different attachments can be, in an example which is however not to be intended as exhaustive, of a plastic material (polyetherimide, polysulfone, polyarylamide, or the like) reinforced with glass or carbon fibre, in such a way as to combine mechanical resistance and sterilization with low costs.

For the connector a simple stainless steel of the AISI 300 class can be employed, or an aluminium alloy or a titanium alloy.

Moreover, it is noted that the particularity of the design of the attachments and the absence of restricted tolerances suggest the adoption of three-dimensional printing techniques.

An advantage of the above-described clamp results from the unusually reduced number of components: a connector and two attachments, with the nut which is preferably integral with the second attachment. The construction and storage costs are thus reduced, as well as the assembly complexity during manufacturing.

Further features and advantages will be more apparent from the following detailed description of a preferred, but not exclusive, embodiment, of the present invention, with reference to the attached figures given by way of non-limiting examples.

BRIEF DESCRIPTION OF THE DRAWINGS

FIG. 6 shows a perspective view of a second alternative of a second attachment which is part of the clamp for an orthopaedic fixator according to the present invention;

FIG. 7 shows an exploded perspective view of the attachment of FIG. 6;

FIG. 8 shows an exploded perspective view, cut away along a median plane, of the attachment of FIG. 6;

DETAILED DESCRIPTION

Figure 18:
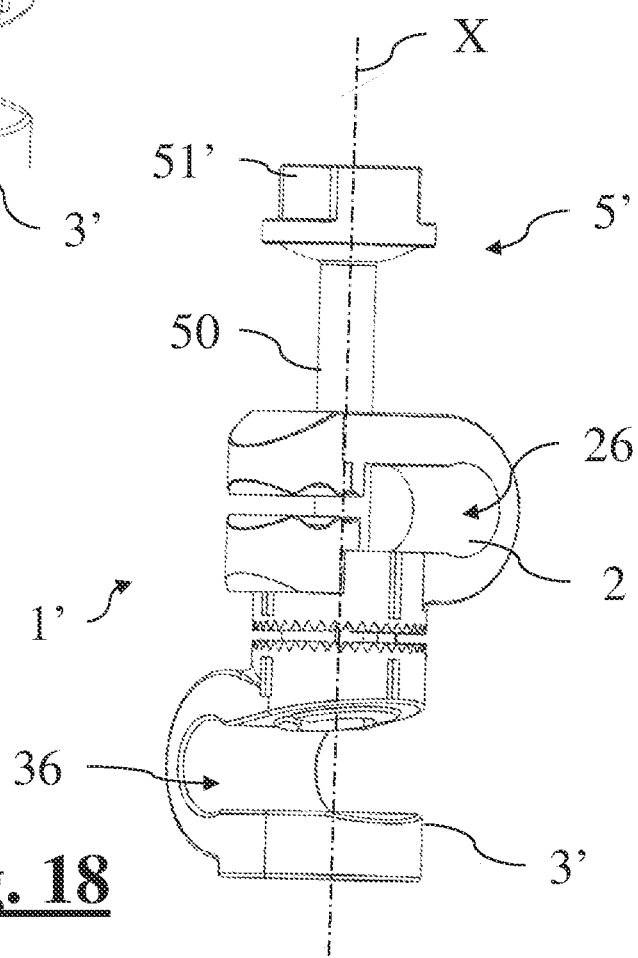
FIG. 18 shows a perspective view of the clamp of FIG. 17 in the open configuration.
Figure 19:
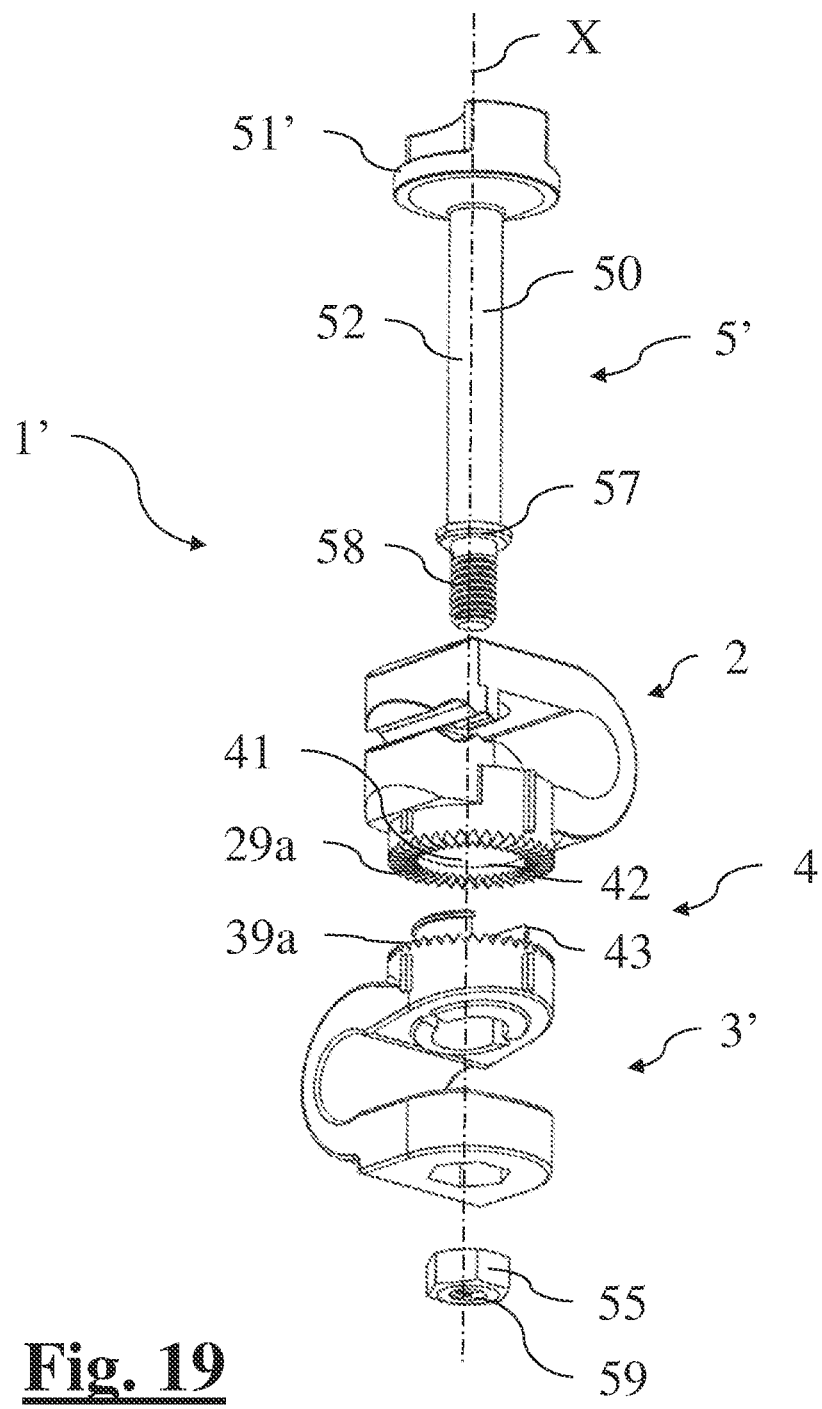
FIG. 19 shows an exploded perspective view of the clamp of FIG. 17.
Figure 20:
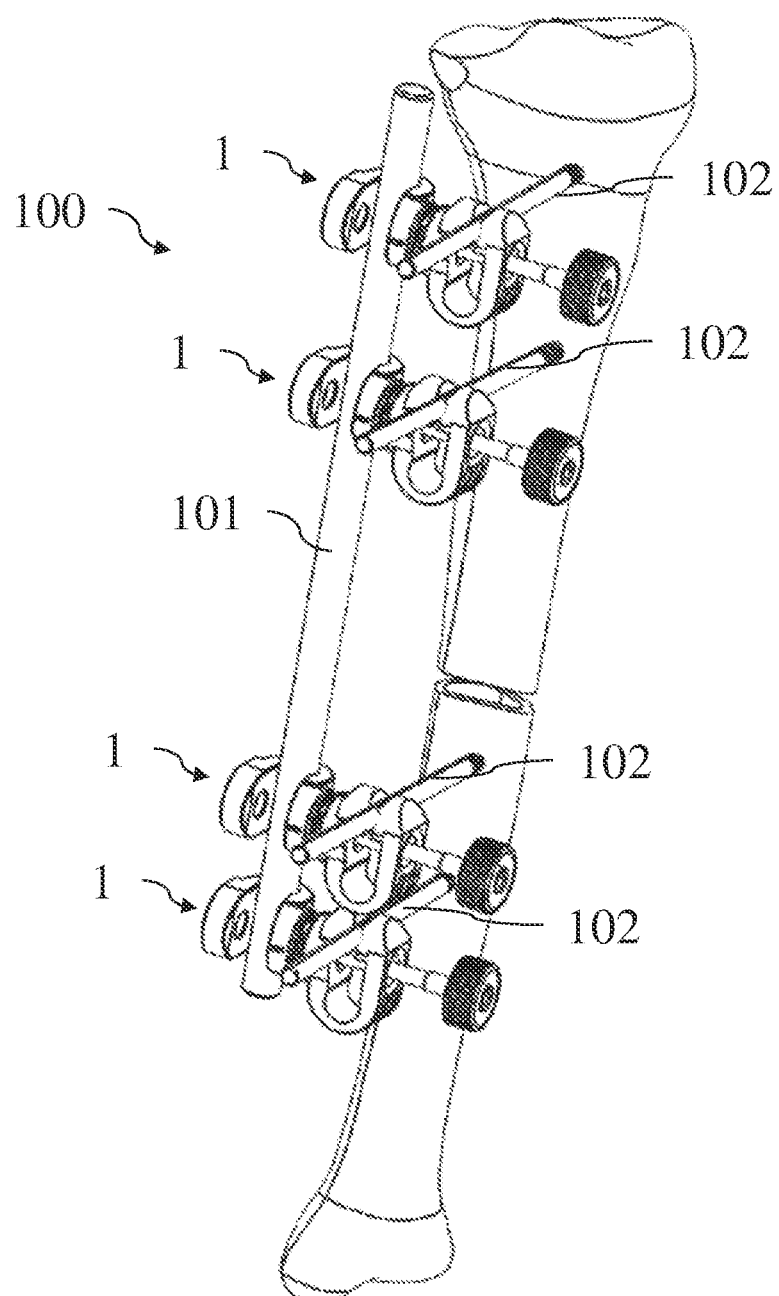
FIG. 20 shows an external fixator, comprising four clamps of the type in FIG. 12, a bar and four bone screws, coupled to the long bone of a patient; the four clamps are shown in the open configuration.
Figure 21:
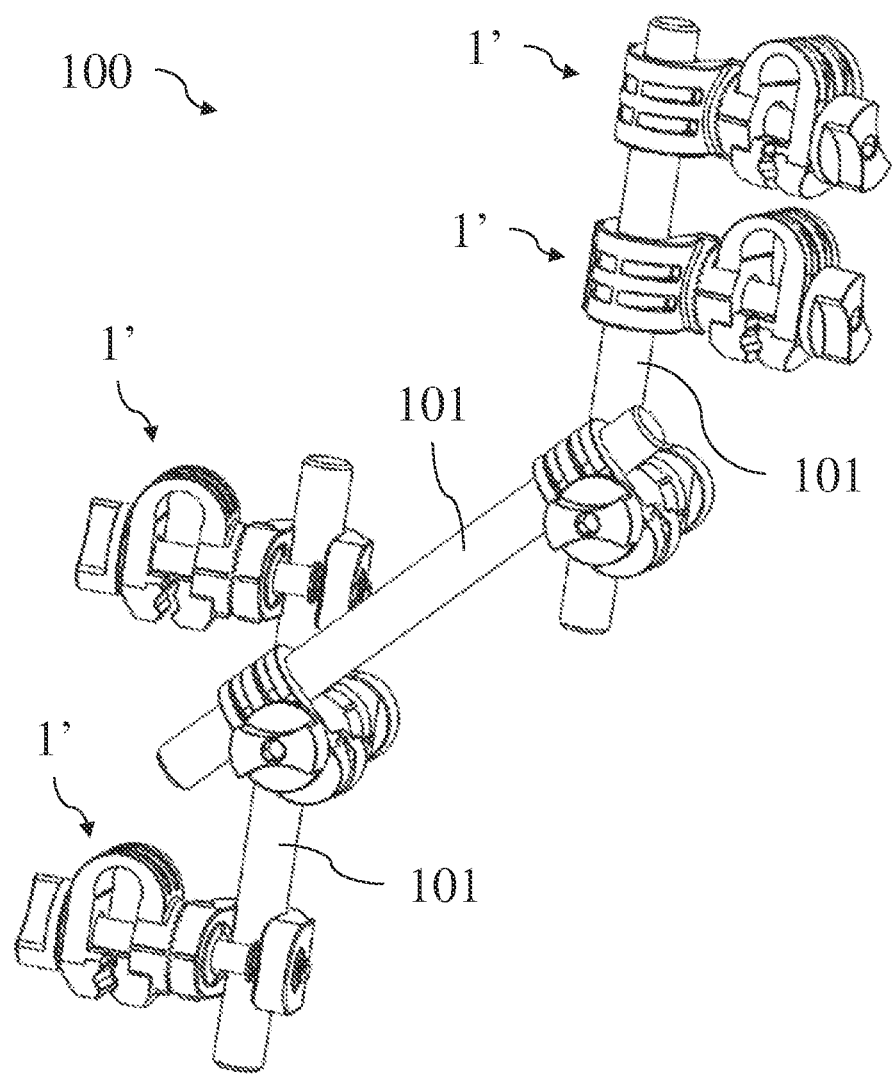
FIG. 21 shows an external fixator comprising six clamps of the type in FIG. 17 and three bars.

With reference to the attached FIGS. 12-19 two alternatives of a clamp designed to act as a connecting element of an external orthopaedic fixator 100, in particular of a quick fixator of the type illustrated in FIGS. 20 and 21, are identified with 1 and 1'. The clamp 1; 1' is arranged to perform in a quick and efficient manner a temporary rigid connection between two connecting bars 101 or between a bar 101 and a bone screw 102, of a diameter of 4 mm, 5 mm or 6 mm.

Both alternatives of the clamp 1; 1' comprise a first attachment 2 and a second attachment 3; 3' held together by a connector 5; 5'; they differ from each other by the adoption of similar but non identical alternatives of the second attachment 3; 3' and of the connector 5; 5'. Other alternatives of the clamp can result from different combinations of the first attachment 2, second attachment 3; 3' and connector 5; 5'.

A first alternative of the connector 5, which can be seen in the overall FIGS. 12-16, comprises a stem 50 provided with a threaded portion 58 at an end thereof. The opposed end of the stem 50 provides a head 51 jointed to the stem by means of a concave surface 52, having a spherical shape.

The threaded portion 58 of the stem 50 is separated from the consecutive unthreaded portion by means of a stop collar 57, i.e. a circular flange with a truncated conical side surface which is inserted into a corresponding seat of the second attachment 3; 3'. The stop collar 57 defines a limit stop which limits the maximum tightening of the connector 5; moreover, as it will better appear from the following description, the same stop collar 57 performs the holding of the connector 5 in the sliding seat thereof on the clamp 1; 1'.

The head 51 provides an externally-knurled ring nut, which defines a gripping portion 54 for the manual preliminary tightening of the connector 5. Internally, separated from the gripping knob 54 by an open cavity 56 in the opposite direction to the stem 50, a coupling profile 53 is arranged, namely a hexagonal recess for a setscrew wrench.

Figure 9:
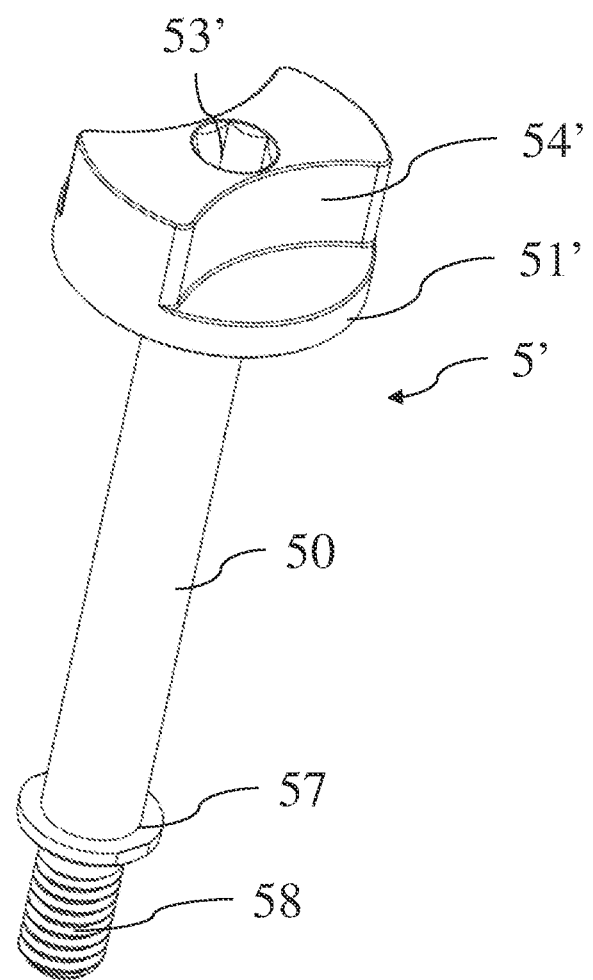
FIG. 9 shows a perspective view of a second alternative of a connector which is part of the clamp for an orthopaedic fixator according to the present invention.
Figures 10, 11:
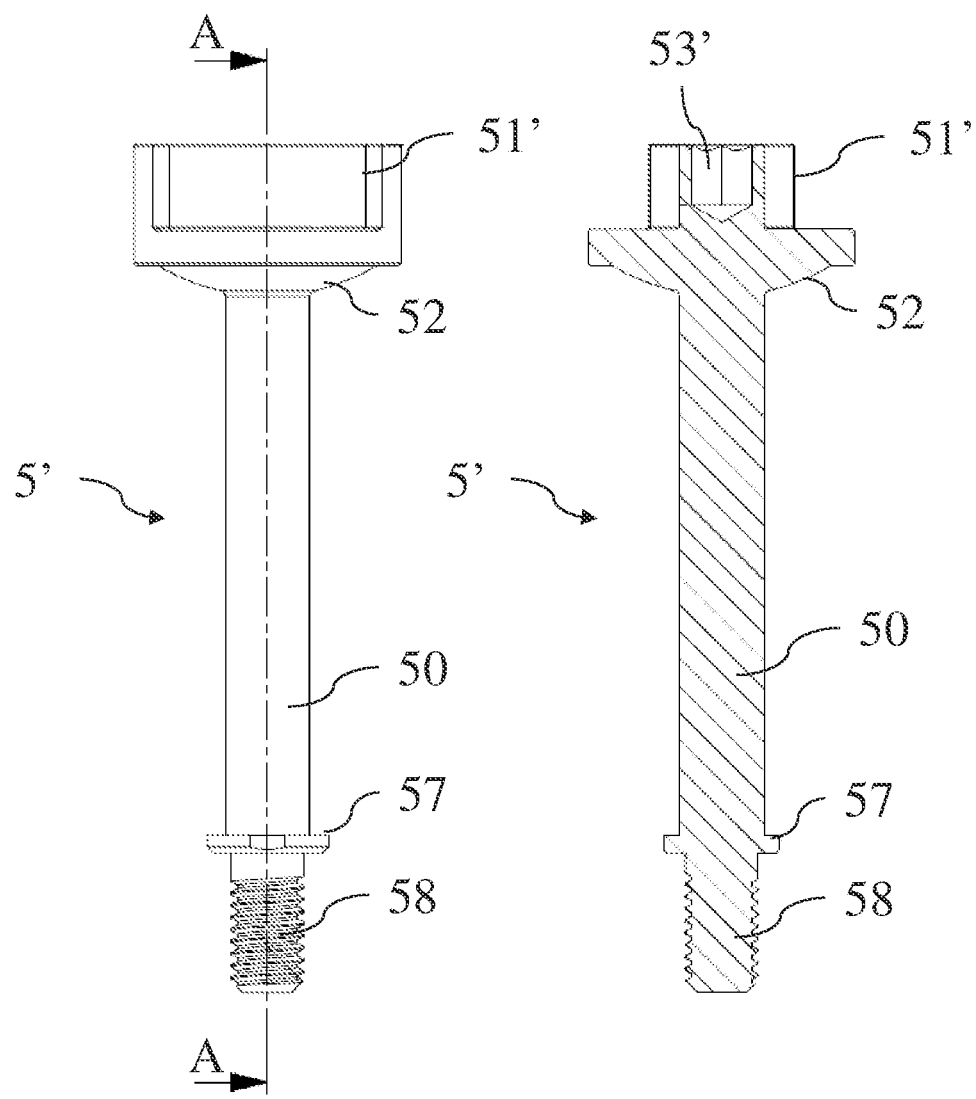
FIG. 10 shows a side view of the connector of FIG. 9.
FIG. 11 shows a front view of the connector cut away along the plane A-A of FIG. 10.
Figure 12:
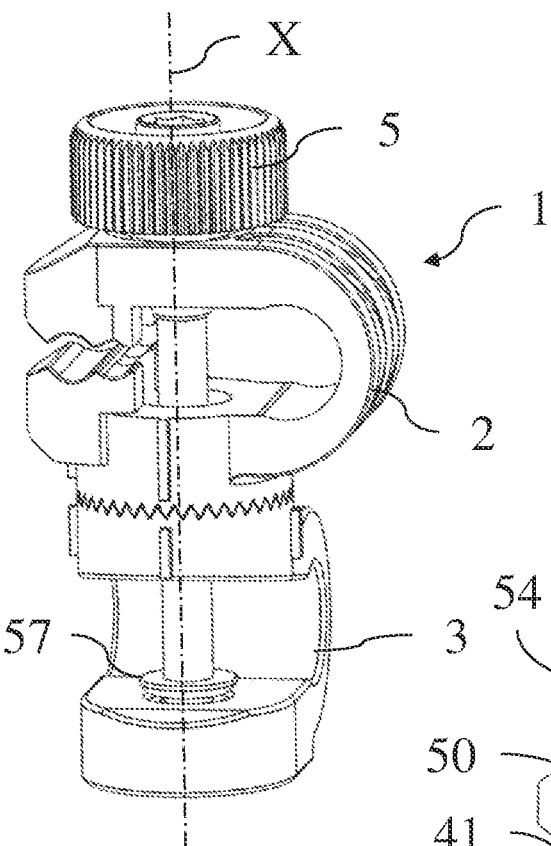
FIG. 12 shows a perspective view of a clamp for an external fixator according to the present invention, comprising: a first attachment of FIG. 1, a second attachment according to the first alternative of FIG. 4 and a fixator according to a first alternative not represented in the previous figures.
Figure 13:
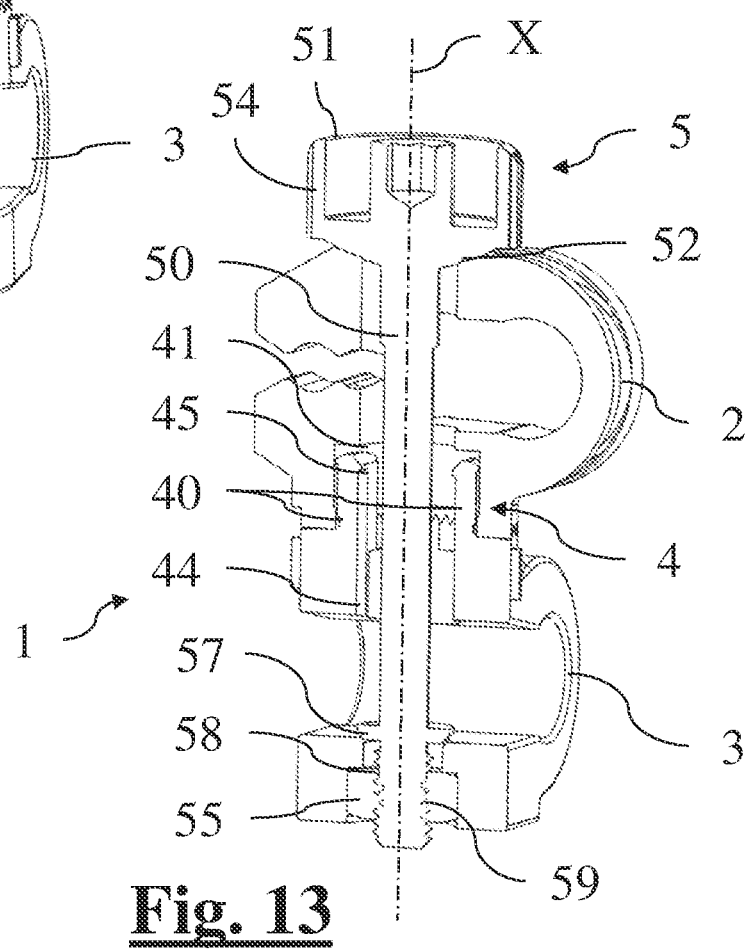
FIG. 13 shows a perspective view, cut away along a median plane, of the clamp of FIG. 12 in the tightened configuration.
Figure 14:
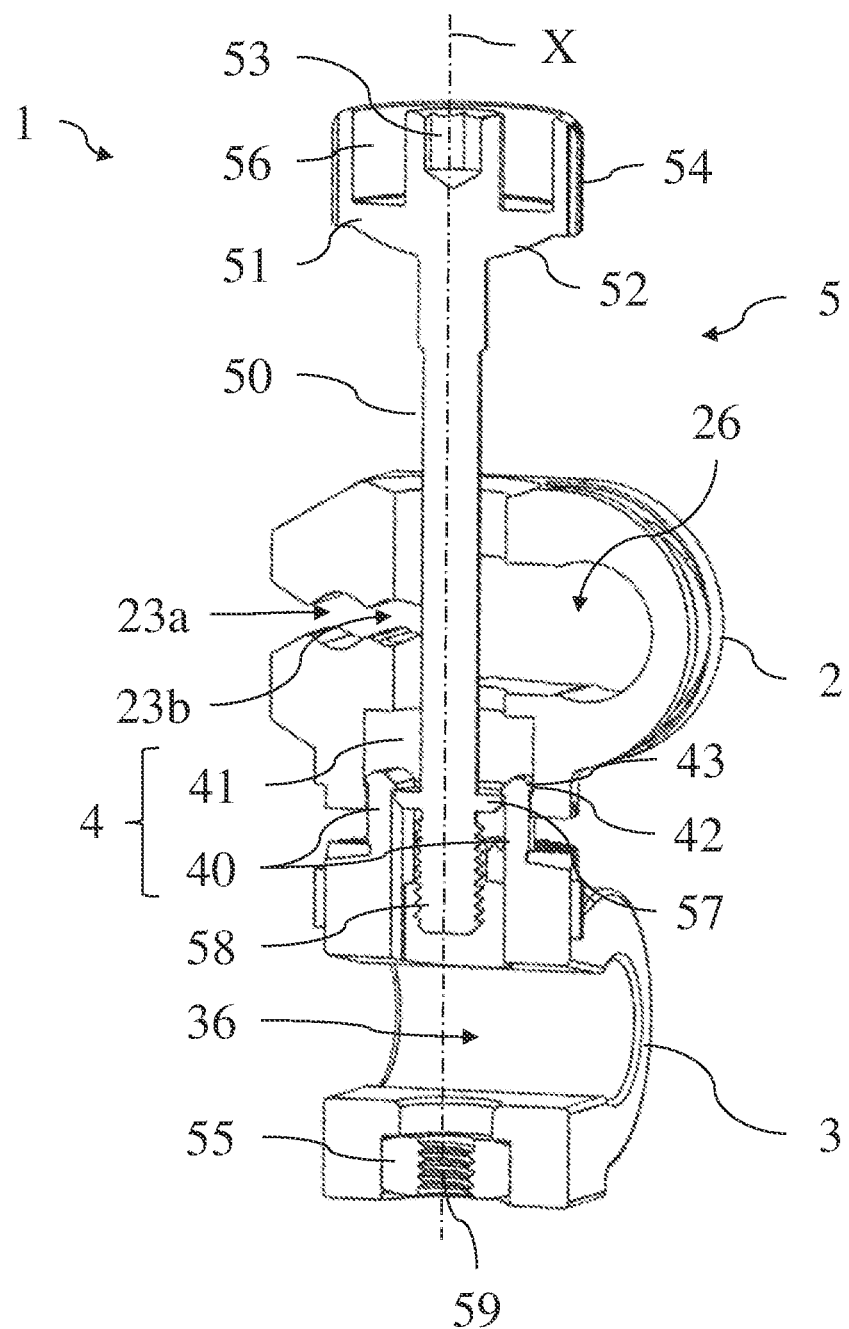
FIG. 14 shows a perspective view, cut away along a median plane, of the clamp of FIG. 12 in the open configuration.
Figure 15:
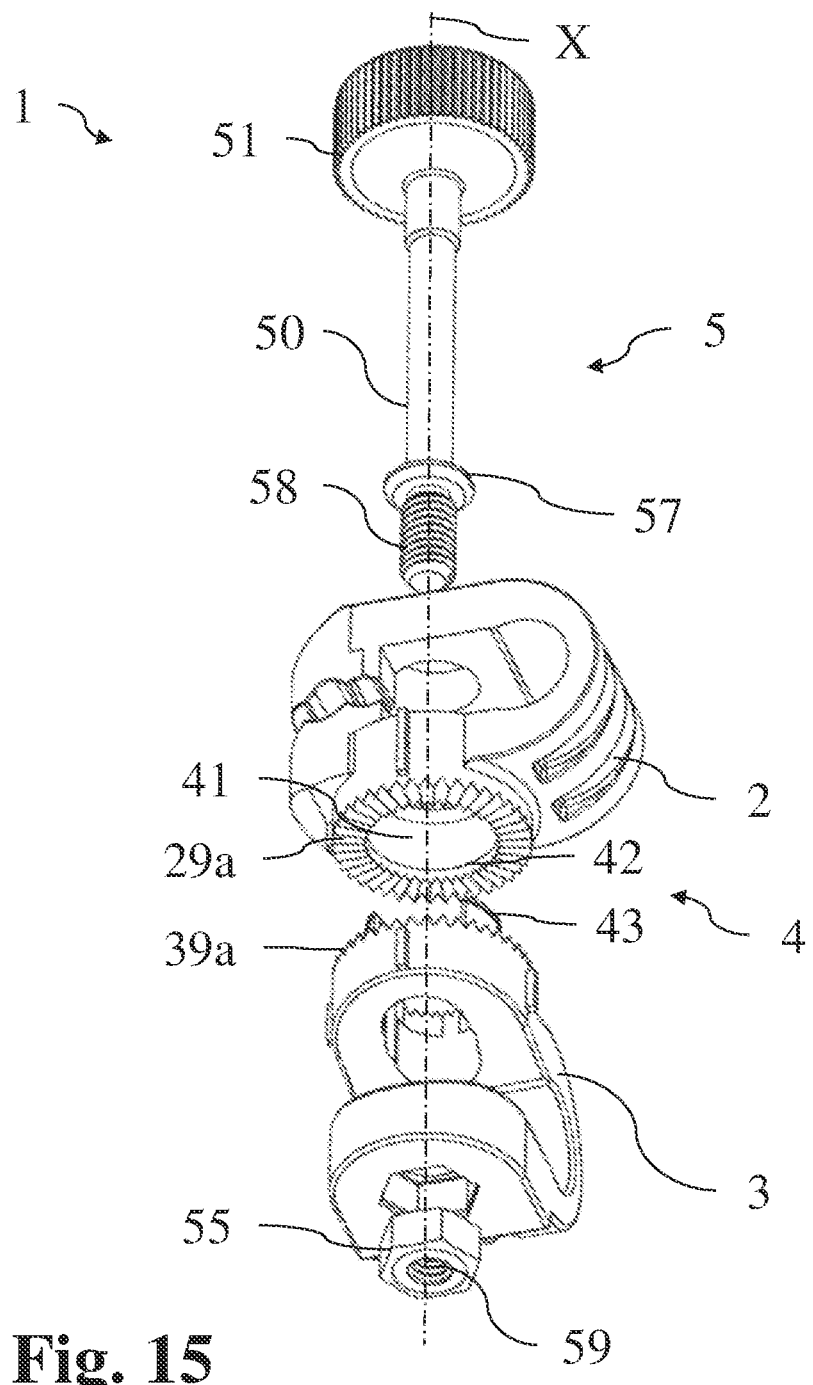
FIG. 15 shows an exploded perspective view of the clamp of FIG. 12.
Figure 16:
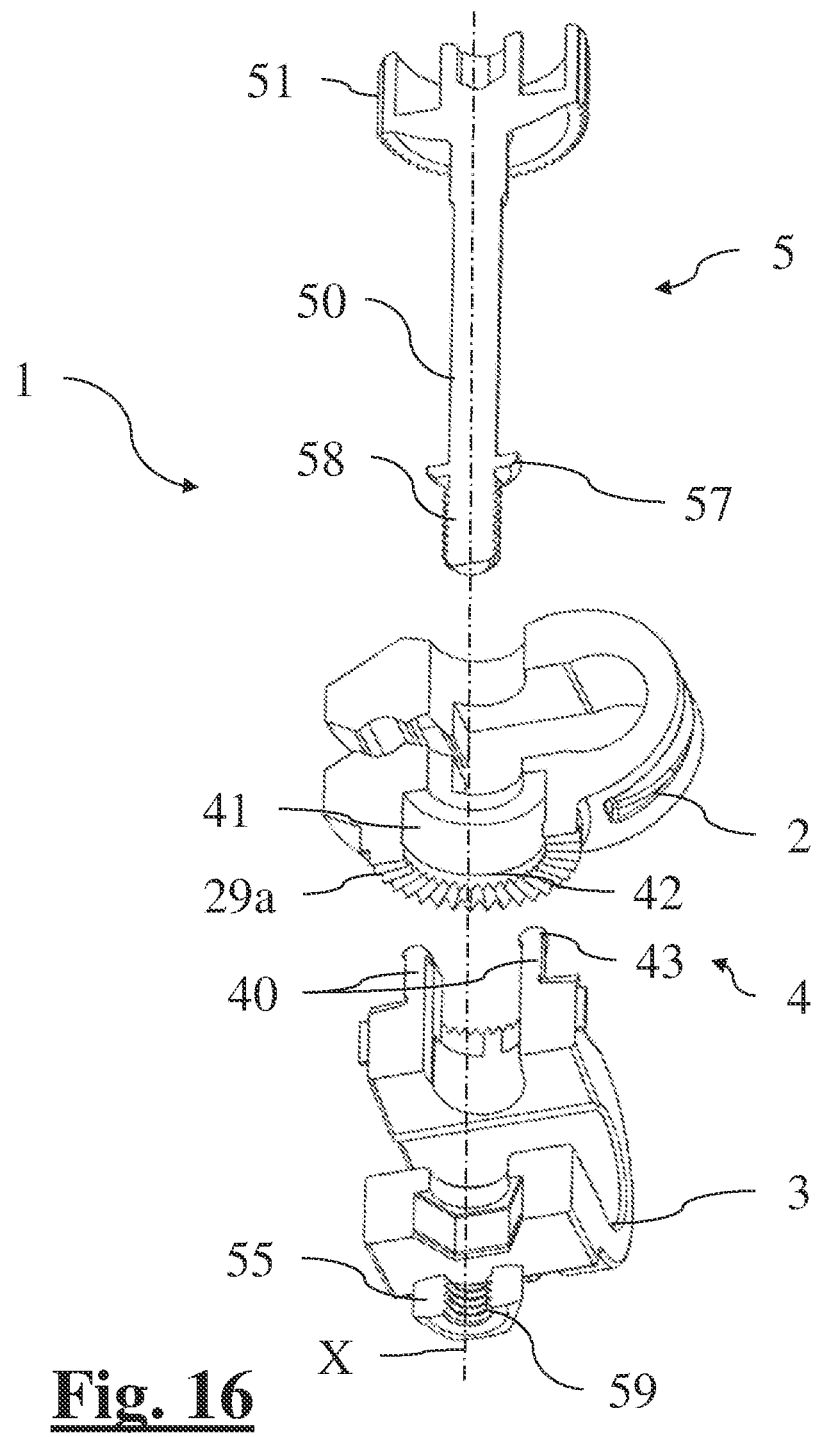
FIG. 16 shows an exploded perspective view, cut away along a median plane, of the clamp of FIG. 12.
Figure 17:
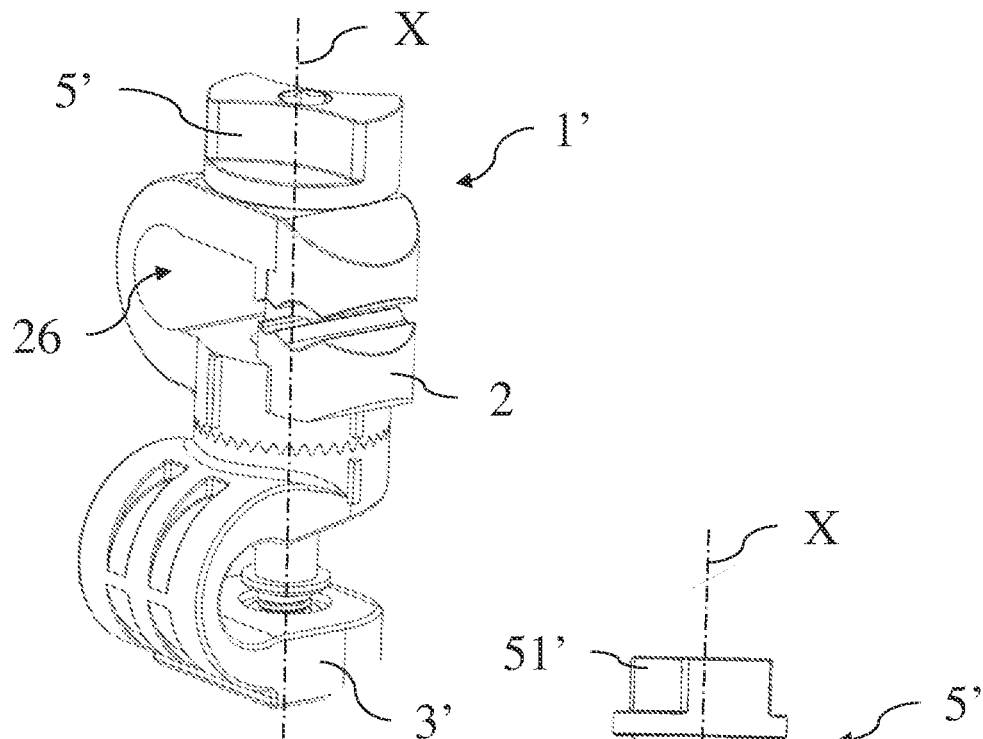
FIG. 17 shows a perspective view of a clamp for an external fixator according to the present invention, comprising: a first attachment of FIG. 1, a second attachment according to the second alternative of FIG. 6 and a fixator according to the second alternative of FIG. 9; the clamp is shown in an intermediate configuration between the tightened configuration and the open configuration.

A second alternative of the connector 5', individually shown in FIGS. 9-11 and which is part of the assembly of FIGS. 17-19, is substantially similar to the previous one except for the shape of the head 51'.

In this case, the head 51' provides indeed a biconcave gripping portion 54', which overhangs a disc-shaped portion defining a diametrically extended gripping element. This gripping portion 54' has, in a central portion, a coupling profile 53' with a hexagonal recess for a setscrew wrench which is similar to the one described above for the first alternative.

The presence of a gripping portion 54; 54' and of a coupling profile 53; 53' separated in the above-described connectors 5; 5' allows a first manual tightening operation, which can be improved afterwards by means of a suitable tightening tool.

The aforesaid connectors 5; 5' screw in a tightening nut 55 which defines a threaded seat 59 therein. The nut 55 is located at an end of the clamp 1; 1' which is opposed to the one of the head 51; 51' of the connector 5; 5'. Screwing in the nut 55, the connector 5; 5' is tightened by packing the interposed attachments 2, 3; 3'.

As it will better come out herebelow, the nut 55 is preferably made integral with the second attachment 3; 3'.

Figure 1:
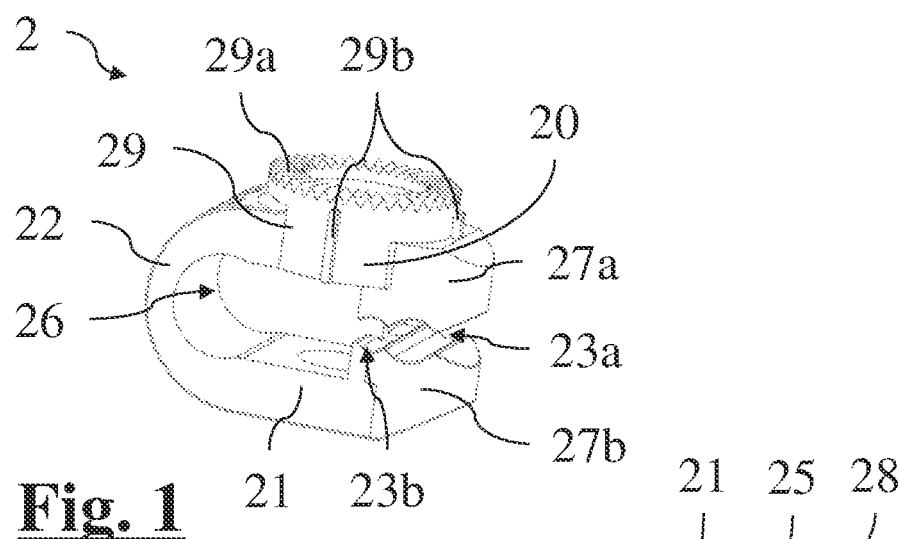
FIG. 1 shows a perspective view of a first attachment which is part of the clamp for an orthopaedic fixator according to the present invention.
Figure 2:
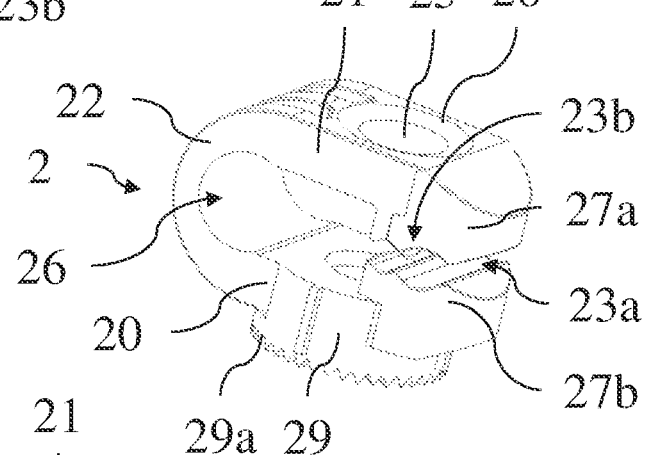
FIG. 2 shows a perspective view, according to a different angulation, of the attachment of FIG. 1.
Figure 3:
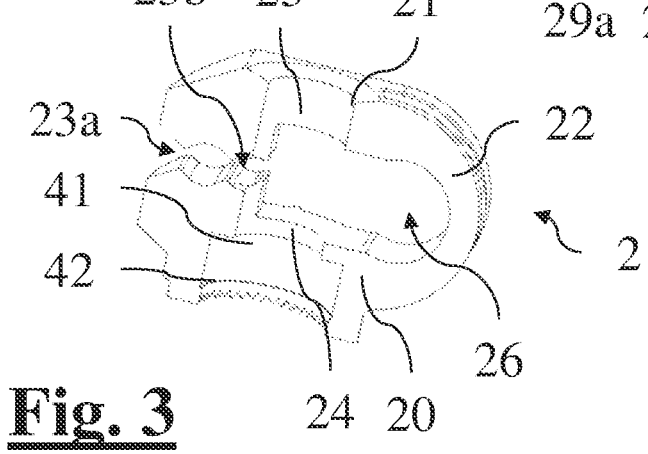
FIG. 3 shows a perspective view, cut away along a median plane, of the attachment of FIG. 1.

The first attachment 2, individually shown in FIGS. 1-3, is provided with two arms, which will be identified as internal 20 and external 21, respectively, with respect to the overall structure of the assembled clamp 1. The arms 20, 21 are connected by a C-shaped flexible bridge 22, i.e. by an elastic hinge which allows the bending thereof outside a rest configuration of mutual parallelism.

The flexible bridge 22 has internally a cylindrical surface, which develops on an arc which is slightly higher than 180° to join then with the internal planar surfaces of the two arms 20, 21. This surface defines a bar housing seat 26, inside which a connecting bar 101 of the external fixator 100 can be tightened.

At the opposed end with respect to the flexible bridge 22, the arms 20, 21 define respective jaws 27a, 27b. These jaws 27a, 27b, which are thickened with respect to the rest of the arm, have opposed surfaces. On each of said surfaces two V-shaped grooved are obtained, extended transversely to the attachment. The grooves, facing the ones of the opposed jaw, define two screw housing seats 23a, 23b. The first screw housing seat 23a, in a more external position with respect to the attachment 2, is arranged to house screws of 5 mm or of 6 mm, depending on the bending imparted to the arms by tightening the connector 5; 5'. The second screw housing seat 23b, in an a more internal position, is instead arranged to house screws of 4 mm. Hence the surgeon selects the housing seat 23a, 23b to be used depending on the diameter of the screw.

Moreover, the internal arm 20 and the external arm 21 comprise respective internal 24 and external 25 holes, arranged for the passage of the stem 50 of the connector 5. These holes 24, 25 are enlarged with respect to the diameter of the stem 50, to allow a clearance which is sufficient to favour the bendings of the attachment 2.

Outside the external passage hole 25 a spherical flaring is made, i.e. a convex seat 28 for the concave surface 52 of the connector 5; 5', which rest on it with substantial contact also under conditions of non-perpendicularity of the external arm 21 with respect to the stem 50.

Finally, it is noted that the internal arm 20 is defined, in an intermediate portion thereof, by a cylindrical bush 29. This bush exhibits a radial toothing 29a arranged to engage against a corresponding toothing of the juxtaposed attachment, ensuring the bending stability of the clamp 1. Moreover, projections 29b are provided on the external surface, which are angularly equally spaced, namely at 90°, which are usable as angular references to ensure the perpendicularity between connecting bars 101 and bone screws 102.

Inside the cylindrical bush a cylindrical coupling seat 41 is defined, which extends below the portion of the arm 20 crossed by the internal passage hole 24. The coupling seat 41 has an orifice which is open towards the second attachment 3; 3' and bordered by a stepwise narrowing 42.

Figure 4:
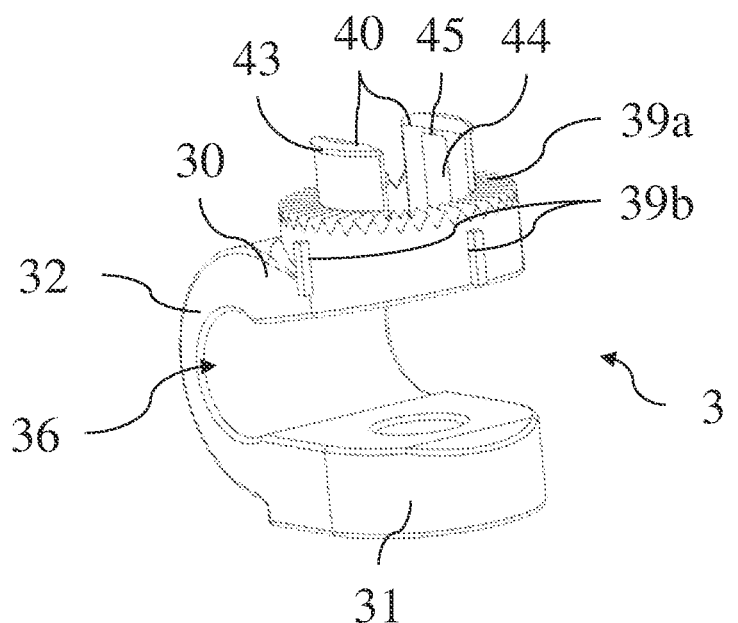
FIG. 4 shows a perspective view of a first alternative of a second attachment which is part of the clamp for an orthopaedic fixator according to the present invention.
Figure 5:
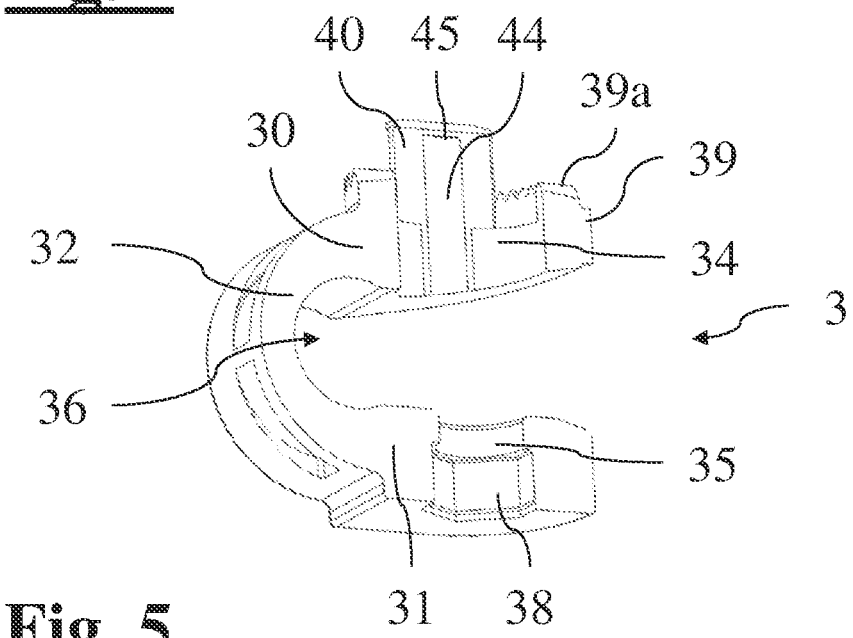
FIG. 5 shows a perspective view, cut away along a median plane, of the attachment of FIG. 4.

A first alternative of the second attachment 3 is individually shown in FIGS. 4-5.

The second attachment 3 has a similar structure to the one of the first attachment 2, except for the differences discussed herebelow.

First of all, the second attachment 3 is not provided with the jaws which define the seat for the bone screw. It is also provided with two arms, internal 30 and external 31 ones with respect to the overall structure of the assembled clamp 1, connected by a C-shaped flexible bridge 32.

The flexible bridge 32 defines in this case too a bar housing seat 36, inside which a connecting bar 101 of the external fixator 100 can be tightened.

The two arms 30, 31 comprise the respective holes 34, 35 arranged for the passage of the stem 50 of the connector 5; in this case too they have an enlarged diameter with respect to the diameter of the stem 50.

Outside the passage hole 35 a hexagonal recess 38 is made for housing the tightening nut 55, which, as previously mentioned, can be embedded in the attachment 3 for example by co-moulding or coupling.

In this case too, the internal arm 30 is defined, in an end and non-intermediate portion, by a cylindrical bush 39. This bush exhibits a radial toothing 39a arranged to engage against the toothing of the juxtaposed attachment and reference projections 39b spaced apart by 90° with respect to each other.

Differently from the first attachment, the cylindrical bush 39 does not define however a coupling seat therein.

Above the cylindrical bush 39, two opposed tongues 40 rise instead sideways with respect to the internal hole 35. These tongues 40 define, together with the above-described coupling seat 41, auxiliary connection means 4 whose function will be explained hereinafter in the present description.

The section of each single tongue 40 defines a circular segment; the tongue 40 has hence an external cylindrical surface which is opposed to a substantially planar internal surface. The end of the external surface is overlapped by an outward-projecting flange, which defines a side tooth 43 of the tongue.

The tongues 40 and the teeth 43 are so sized as to allow the tongues 40 to be snap-introduced into the coupling seat 41 with the respective narrowing 42. Once introduced, the tongues 40 can slide in the cylindrical volume defined by the coupling seat 41. The teeth 43, going to abut against the narrowing 42, prevent in this case the extraction of the tongues 40, thus constraining the second attachment 3 to the first attachment 2. In the constrained position, a relative axial movement between the two attachments 2, 3; 3' is however possible, due to the travel of the teeth 43 within the coupling seat 40. A relative rotational movement between the two attachments 2, 3; 3' with respect to a central axis of rotation X thereof is also possible, due to the cylindrical shape of the tongues 40 and coupling seat 41, wherein the two attachments 2, 3; 3' are sufficiently spaced apart to avoid the mutual engagement of the radial toothings 39a, 39b.

The tongues 40 are suitably flexible. The maximum deviation of the two attachments 2, 3; 3' engaged with each other allows an operator to access the tongues 40, deforming them inwards and disengaging the teeth 43 from the narrowing 42. The disconnection of the two attachments 2, 3; 3' is thus performed.

The internal surface of the tongues 40 defines a cylindrical track 44 which is open inwards of the attachment 3. Said track is discontinued above by a limit stop 45. Once the clamp is assembled, the external periphery of the stop collar 57 can slide in the cylindrical track 44 up to abut against the limit stop 45, which prevents the complete extraction of the connector 5; 5'. In order to perform the complete disassembly of the clamp 1; 1', it is first necessary to uncouple the tongues 40 from the coupling seat 41. The tongues 40, no more constrained within the coupling seat 41, can thus deform outwards releasing the stop collar 57 of the connector 5; 5'.

A second alternative of the second attachment 3', individually shown in FIGS. 6-8, is substantially identical to the first one except that the tongues 40 are made on an insert 46. This insert 46 comprises a flanged common base which is introduced with interference into the internal hole 34 of the cylindrical bush 39. The flange abuts against the lower surface of the internal hole 34 defining the correct locking position.

The above-described clamps 1; 1' can also take, besides the traditional tightened configuration in which the tightened fixator 5; 5' locks the bars 101 and/or the bone screws 102 in the desired position, an open configuration which can be used during surgery to sideways introduce a bar 101 into the housing seats 36 of the second clamp 3; 3'; for example to check the alignment of a plurality of clamps to be connected with the bar 101, as illustrated in the attached FIG. 20.

This open configuration provides that the threaded portion 58 of the connector 5; 5' is disengaged from the nut 55, and extracted until the stop collar 57 reaches the limit stop 45 defined inside the tongues 40. In this configuration, the connector 5; 5' frees therefore completely the side entrance to the housing seat 36 of the second clamp 3; 3'. The first 2 and second clamp 3; 3', no more held by the threaded connection, are however kept cohesive by the auxiliary connection means 4, which, as discussed above, allow the relative rotation along the axis of rotation X between the two components of the clamp 1; 1'.

Obviously, a person skilled in the art, in order to meet contingent and specific requirements, will be allowed to bring several modifications and alternatives to the above-described invention, all however comprised in the scope of protection of the invention as defined by the following claims.

The invention claimed is:

1. A clamp for an external fixator, comprising:
at least one first attachment provided with at least one bar housing seat for a bar of the external fixator or with at least one screw housing seat for a bone screw;
at least one second attachment provided with at least one bar housing seat or at least one screw housing seat; and
a connector which extends along a connector axis and which, in a tightened configuration, passes through said first attachment and said second attachment making them integral with each other and locking the bar or bone screw, the connector comprising a head which is accessible to a user at a first end of the clamp and a stem provided with at least one threaded portion, said clamp comprising a threaded seat located at a second end thereof, the first end of the clamp being on a side of the first attachment and the second end of the clamp being on a side of the second attachment, the second attachment comprising two arms connected by a C-shaped flexible bridge which defines the bar housing seat or the screw housing seat, wherein, in the tightened configuration, the stem passes through said first attachment and said second attachment, the threaded portion engages in the threaded seat, and said stem extends between the two arms interfering with a side entrance to the bar housing seat or the screw housing seat of the second attachment, locking the bar or the bone screw within the bar housing seat or the screw housing seat of the second attachment,
said clamp being further configurable in an open configuration, wherein said threaded portion is totally disengaged from the threaded seat, said connector is at least partially extracted from said second attachment, and said stem rises in a direction of the first attachment, thus freeing a side entrance to said bar housing seat or said screw housing seat;
the clamp further comprising an auxiliary connection which keeps said first attachment and said second attachment interconnected in said open configuration, wherein said auxiliary connection limits a relative displacement along the connector axis between said first attachment and said second attachment up to a maximum offset.

2. The clamp for an external fixator according to claim 1, wherein said connector comprises a stop collar arranged along the stem to limit the maximum tightening of the clamp.

3. The clamp for an external fixator according to claim 2, wherein said stop collar prevents the complete extraction of the connector from the rest of the clamp in the open configuration.

4. The clamp for an external fixator according to claim 1, wherein said auxiliary connection allows, in the open configuration, a relative axial movement of the second attachment with respect to the first attachment, between: a first position, in which two coupling surfaces, provided on the first attachment and on the second attachment, respectively, are mutually engaged in contact preventing the relative rotation of the first attachment with respect to the second attachment; and a second position, in which said coupling surfaces are spaced apart and the relative rotation of the first attachment with respect to the second attachment is allowed.

5. The clamp for an external fixator according to claim 4, wherein said auxiliary connection comprises at least one tongue, which is integral with one of the first attachment and the second attachment, and at least one coupling seat which is integral with the other of the first attachment and the second attachment, said at least one tongue being axially sliding within said coupling seat up to reach a maximum extension lock, said at least one tongue being further rotatable within said coupling seat with respect to an axis of rotation.

6. The clamp for an external fixator according to claim 5, wherein said maximum extension lock is defined by a narrowing of the coupling seat against which a tooth protruding outwards of said at least one tongue abuts.

7. The clamp for an external fixator according to claim 6, wherein the at least one tongue comprises a plurality of tongues, arranged along a circumference centred in the axis of rotation, and being deformable inwards to allow a snap coupling within the coupling seat.

8. The clamp for an external fixator according to claim 5, wherein said at least one tongue is integral with the second attachment and defines a lock to the extraction of the connector in the open configuration.

9. The clamp for an external fixator according to claim 1, wherein said auxiliary connection further comprises a maximum extension lock which allows assembly of the first attachment and second attachment along the connector axis but prevents disconnection of the first attachment and second attachment along the connector axis.

10. The clamp for an external fixator according to claim 9, wherein said maximum extension lock comprises elastic prongs having profiled teeth at their free ends.

\* \* \* \* \*